(12) United States Patent
Itoh (10) Patent No.: US 8,783,441 B2
(45) Date of Patent: Jul. 22, 2014

(54) TRANSPORT SYSTEM AND TRANSPORT METHOD

(71) Applicant: Aoi Seiki Co., Ltd., Kumamoto (JP)

(72) Inventor: Teruaki Itoh, Kumamoto (JP)

(73) Assignee: Aoi Seiki Co., Ltd., Kumamoto-shi, Kumamoto-ken (JP)

( * ) Notice: Subject to any disclaimer, the term of this patent is extended or adjusted under 35 U.S.C. 154(b) by 0 days.

(21) Appl. No.: 13/790,018

(22) Filed: Mar. 8, 2013

(65) Prior Publication Data

US 2013/0233673 A1    Sep. 12, 2013

(30) Foreign Application Priority Data

Mar. 8, 2012    (JP) .................................. 2012-052121

(51) Int. Cl.
    *B65G 33/06*    (2006.01)
(52) U.S. Cl.
    USPC ..................... 198/467.1; 198/459.3; 198/625; 198/663
(58) Field of Classification Search
    USPC ................... 198/625, 459.3, 662, 663
    See application file for complete search history.

(56) References Cited

U.S. PATENT DOCUMENTS

| | | | |
|---|---|---|---|
| 5,040,894 A | | 8/1991 | Karp et al. |
| 5,117,965 A | * | 6/1992 | Newell et al. ................. 198/444 |
| 5,310,043 A | * | 5/1994 | Alcorn .......................... 198/625 |
| 7,159,489 B2 | * | 1/2007 | Itoh ................................. 81/3.2 |
| 2005/0207937 A1 | | 9/2005 | Itoh |
| 2010/0064826 A1 | | 3/2010 | Champseix et al. |

FOREIGN PATENT DOCUMENTS

| | | |
|---|---|---|
| DE | OFF 2256418 | 5/1974 |
| JP | 64-516 | 1/1989 |
| JP | 1-230976 | 9/1989 |
| JP | 2-4816 | 1/1990 |
| JP | 3-288710 | 12/1991 |
| JP | 4-104058 | 4/1992 |
| JP | 4-94315 | 8/1992 |
| JP | 4-365666 | 12/1992 |
| JP | 5-92230 | 12/1993 |
| JP | 9-323810 | 12/1997 |
| JP | 2811232 | 8/1998 |
| JP | 2002-2947 | 1/2002 |
| JP | 2005-263478 | 9/2005 |
| JP | 2008-81288 | 4/2008 |
| JP | 2010-201396 | 9/2010 |

OTHER PUBLICATIONS

JP Official Action and English translation in SN 2012-052121 mailed Aug. 20, 2013.
European Search Report in EP 13 00 0996 dated Aug. 28, 2013.
Official Action and English translation in Korean SN 2013-0024495 mailed Mar. 26, 2014.

* cited by examiner

*Primary Examiner* — Ramya Burgess
*Assistant Examiner* — Lester Rushin
(74) *Attorney, Agent, or Firm* — Nixon & Vanderhye P.C.

(57) ABSTRACT

According to an embodiment, a transport system configured to transport a receptacle which accommodates an upright sample holder containing a sample, the transport system including a screw includes a rotatable shaft disposed along a predetermined transport path and a helical ridge protruding outward from an outer peripheral surface of the shaft, and a drive unit configured to rotate the screw.

2 Claims, 7 Drawing Sheets

TRANSPORT SYSTEM AND TRANSPORT METHOD

CROSS-REFERENCE TO RELATED APPLICATIONS

This application is based upon and claims the benefit of priority from Japanese Patent Application No. 2012-052121, filed Mar. 8, 2012, the entire contents of which are incorporated herein by reference.

BACKGROUND OF THE INVENTION

1. Field of the Invention

Embodiments of the present invention relate to a transport system and a transport method for transporting sample holder receptacles.

2. Description of the Related Art

A belt-drive transport system (e.g., Jpn. Pat. Appln. KOKAI Publication No. 2005-263478) is a known example of a system for transporting sample holders configured to contain samples such as blood. This system comprises a belt, rotating rollers, a feed mechanism such as a motor, and a pair of guide rails. The belt is stretched over a base extending in a transport direction. The rollers are arranged beneath the belt. The feed mechanism rotates the rollers to feed the belt. The guide rails are disposed spaced at the top part of the belt. In the belt-drive transport system of this type, receptacles that accommodate the sample holders are placed on the belt and guided in engagement with the guide rails for transport as the belt moves.

According to the belt-drive transport system described above, the system configuration and maintenance work are so complicated that there is a demand for a simple transport system with high maintenance performance.

BRIEF SUMMARY OF THE INVENTION

According to an embodiment, a transport system configured to transport a receptacle which accommodates an upright sample holder containing a sample, the transport system comprising a screw comprising a rotatable shaft disposed along a predetermined transport path and a helical ridge protruding outward from an outer peripheral surface of the shaft, and a drive unit configured to rotate the screw.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

First Embodiment

Figure 1:
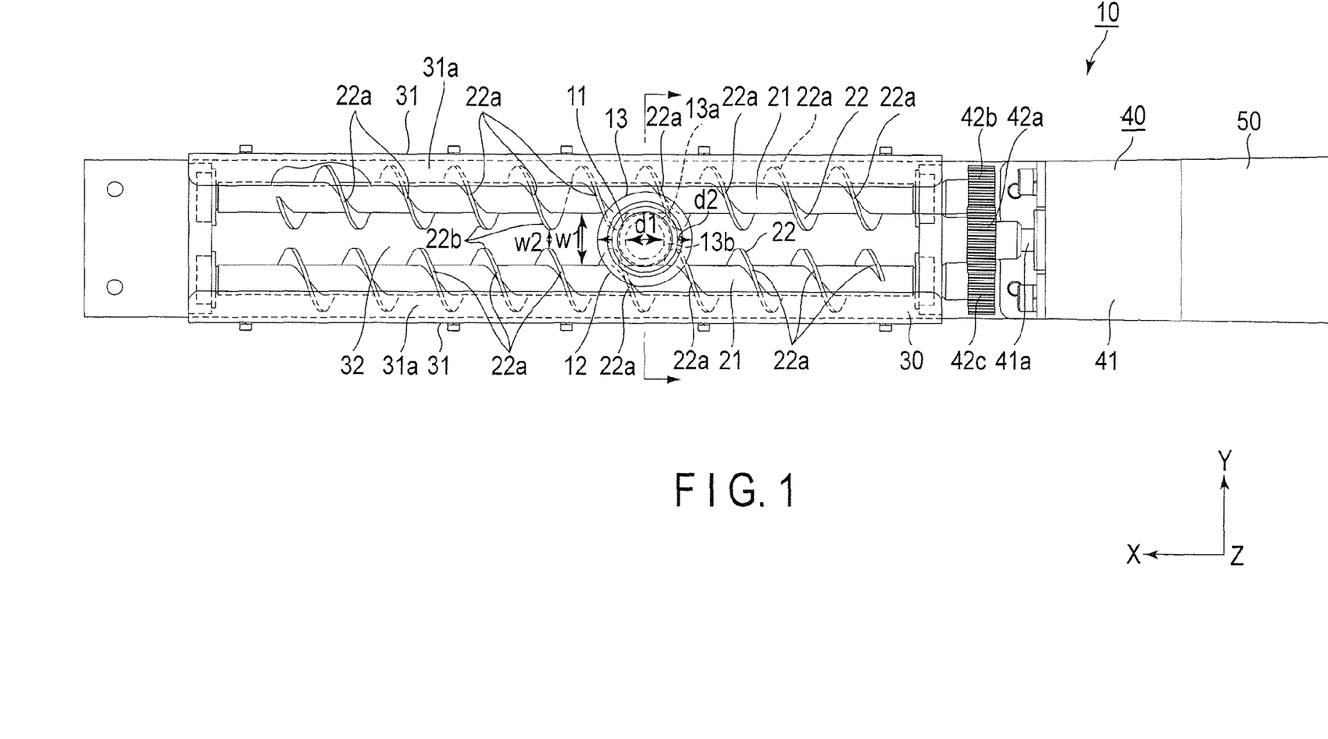
FIG. 1 is a plan view of a transport system according to a first embodiment of the invention.
Figure 2:
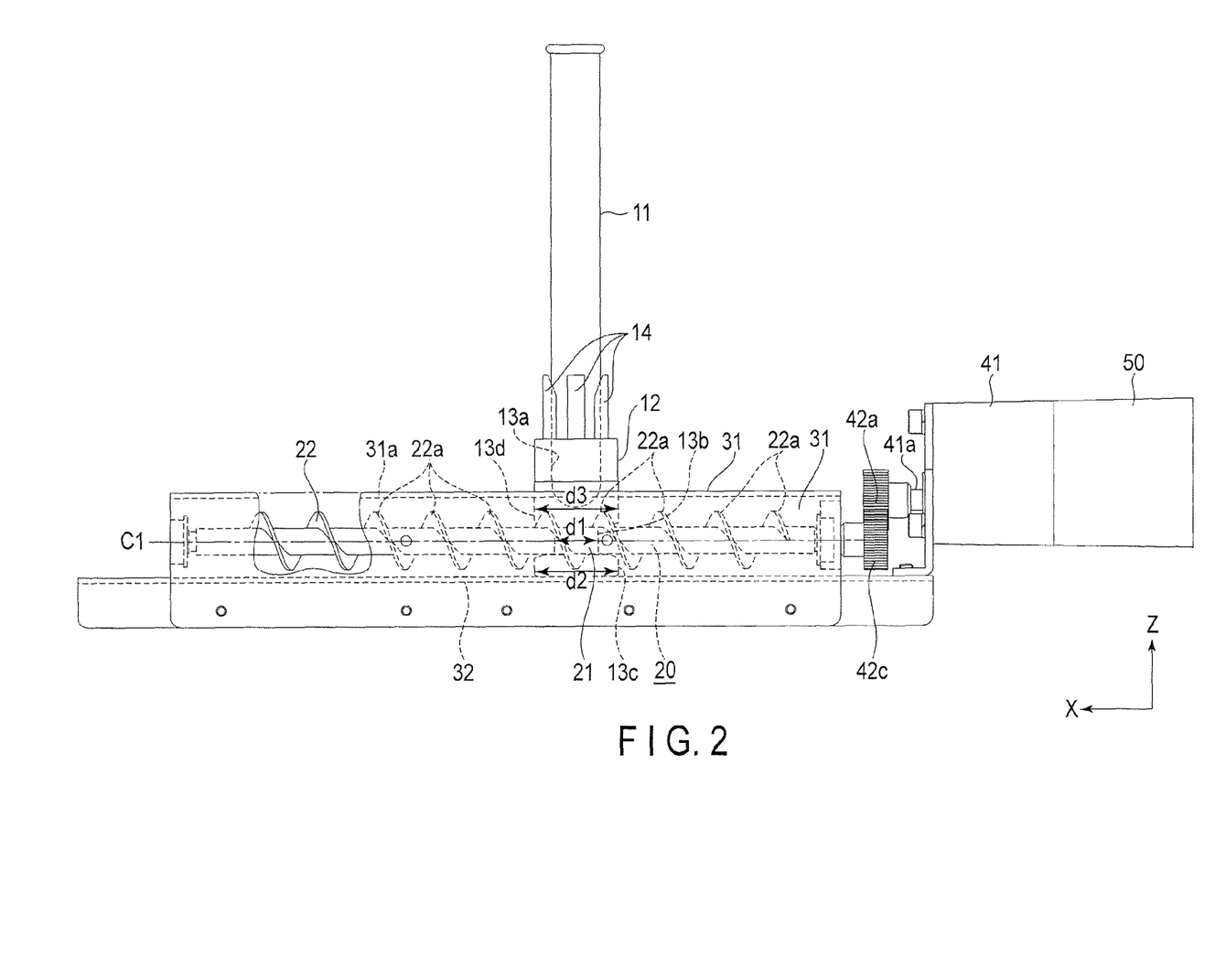
FIG. 2 is a side view of the transport system of the first embodiment.
Figure 3:
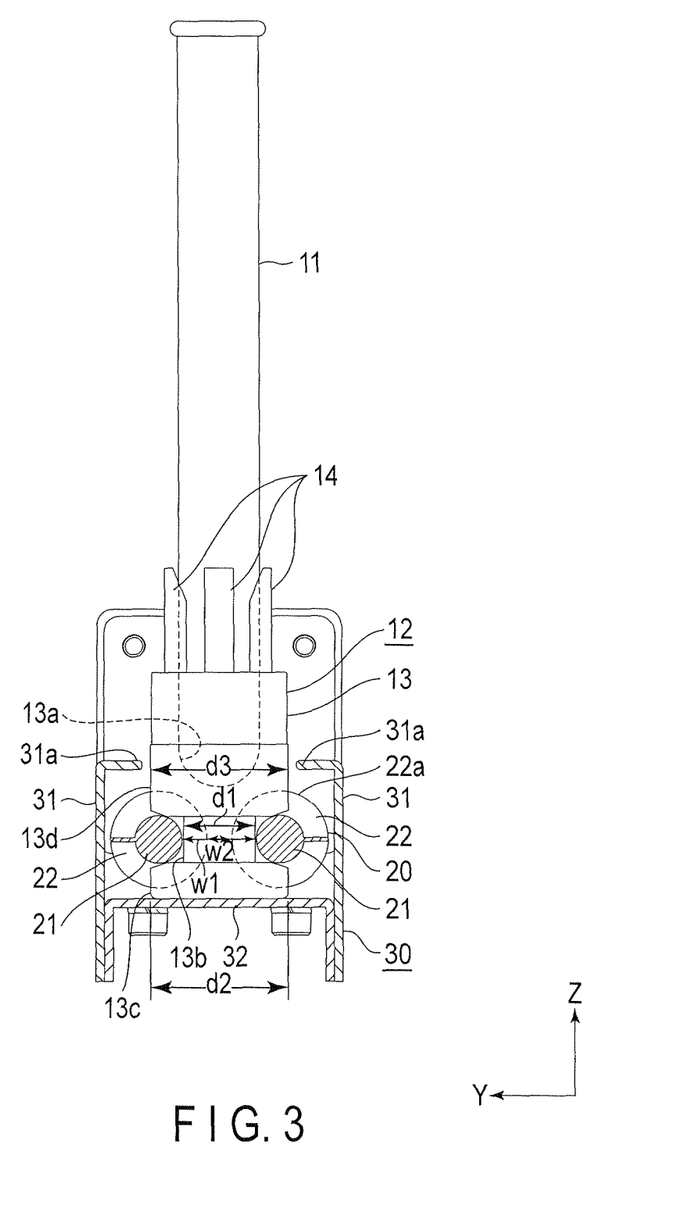
FIG. 3 is a sectional view of the transport system of the first embodiment.

The following is a description of a transport system 10 according to a first embodiment of the invention. FIGS. 1, 2 and 3 are a plan view, side view, and sectional view, respectively, of the transport system 10 of the present embodiment. In these drawings, some structural elements are enlarged or reduced in scale or omitted for ease of illustration, and arrows X, Y and Z indicate three orthogonal directions, individually.

The transport system 10 has the function of transporting a receptacle 12 for accommodating a test tube as a sample holder 11, which contains a sample such as blood, from one end side toward the other end in a transport direction along the arrow X.

The transport system 10 comprises a screw 20, frame 30, drive unit 40, and control unit 50. The screw 20 is located extending along a predetermined transport path. The frame 30 comprises a pair of guide rails 31 disposed spaced on the opposite sides of the screw 20. The drive unit 40 serves to rotate the screw 20. The control unit 50 controls the operation of the drive unit 40. FIG. 1 is a cutaway sectional view showing the internal structure of one of the guide rails 31. In this case, the transport path is set in the direction of the arrow X.

As shown in FIGS. 2 and 3, the receptacle 12 comprises a columnar substrate 13 formed by, for example, resin molding. The substrate 13 is formed with an accommodation section 13a, which opens upward at its axial section. A plurality of receptacle guides 14 are arranged on the inner peripheral surface of the accommodation section 13a. The receptacle guides 14 are urged by urging means, such as springs, so that they can be displaced to increase or decrease the inner diameter of the accommodation section 13a. The sample holder (test tube) 11 is surrounded by the receptacle guides 14 so that it is vertically held in the accommodation section 13a.

A small-diameter annular groove (groove section) 13b is formed on the outer peripheral portion of the substrate 13. Flanges 13c and 13d are formed below and above, respectively, of the annular groove 13b. The flanges 13c and 13d are larger in diameter than the annular groove 13b and constitute a circular outer peripheral surface that projects outward.

Each of the pair of screws 20 shown in FIGS. 1 to 3 is, for example, a molded plastic piece, integrally comprising a shaft 21 extending in the transport direction and a helical ridge 22 protruding radially outward from the outer peripheral surface of the shaft 21.

The shaft 21 is a column rotatable about an axis C1 and coaxial with the transport direction. One end side of the shaft 21 is coupled to the drive unit 40 and configured to rotate under the control of the control unit 50.

The ridge 22 is helically formed on the outer peripheral surface of the shaft 21 so that it can rotate integrally with the shaft 21. The ridge 22 is formed along a single, circumferentially continuous helical line inclined at a predetermined angle to the axis. The ridge 22 is formed spanning between the axially opposite ends of the shaft 21. The ridge 22 is configured to pass around the shaft 21 several times, e.g., ten times in this case. Thus, a plurality (e.g., 10 in this case) of oblique ridge portions 22a that are circumferentially inclined relative to the axis C1 are axially arranged at regular intervals, as viewed from one lateral side of the shaft 21. The ridge portions 22a are part of the ridge 22, that is, the ridge portions 22a form the single continuous helical ridge. Various designs of the screw 20, such as the angle, thickness, and outer diameter of the ridge 22, are set to suitable dimensions for engaging with and propelling a plurality of receptacles 12 at regular intervals.

As shown in FIG. 1, the pair of screws 20 are spaced parallel to each other. The receptacle 12 is supported between the respective ridges 22 of the pair of screws 20 that are arranged transversely relative to the screws. The receptacle 12 is held between the ridge portions 22a that are axially arranged on the respective shafts 21 of the screws 20. In this arrangement, the annular groove 13b of the receptacle 12 is engagingly sandwiched between the pair of shafts 21.

For example, a distance W1 between the pair of screws 20 is set to be slightly greater than a diameter d1 of the annular groove 13b, and a distance W2 between respective edges 22h of the ridges 22 of the screws 20 to be slightly smaller than diameter d2. Further, respective diameters d2 and d3 of flanges 13c and 13d are set to be greater than distance W1 between the shafts 21.

Thus, the receptacle 12 is configured so that the flanges 13c and 13d are sandwiched axially and transversely between the pair of ridge portions 22a and the annular groove 13b is sandwiched between the shafts 21, whereby the substrate 13 is held between the screws 20.

As the pair of screws 20 rotate, they are axially pushed by the rotating ridges 22, and the sample holder 11 in each receptacle 12 is fed to the distal end side. When this is done, the annular groove 13b is sandwiched between the shafts 21 on the opposite sides, and the longitudinally and transversely opposite sides of the flanges 13c and 13d between the ridge portions 22a. Thus, the receptacle 12 is guided by the axially extending transport path.

The frame 30 is made of a plastic or aluminum material and comprises two opposite guide rails 31 located individually on the opposite sides of the transport path and a plate-like base 32 formed along the transport path. The pair of guide rails 31 are located opposite each other so that an opening capable of accommodating the receptacle 12 is formed at the top and is secured to the base 32. Longitudinally extending guide ribs 31a protrude individually inward from the respective upper end edges of the guide rails 31.

The drive unit 40 comprises a motor 41 and transmission mechanism 42. The transmission mechanism 42 comprises a plurality of gears that transmit the torque of a drive shaft 41a of the motor 41. The shaft of a first gear 42a is coupled to the drive shaft 41a of the motor 41. The respective shafts 21 of the screws 20 are coupled individually to the respective shafts of second and third gears 42b and 42c, which individually engage with the gear 42a.

As shown in FIGS. 1 to 3, the bottom of the substrate 13 of the receptacle 12 is placed on the base 32, and the receptacle 12 is engagingly supported between the pair of screws 20 for movement in the transport direction.

If the motor 41 is rotated in this supported state, the screws 20 rotate so that the continuous helical ridges 22 rotate. Thereupon, the ridge portions 22a, which are arranged at regular intervals as viewed from above, are displaced so that they move axially. The receptacle 12 is axially fed by means of the feed function of the ridges 22 based on the rotation of the screws 20. Thus, the receptacle 12 slidingly moves on the shafts 21, held between the shafts 21 and between the ridge portions 22a, as it is fed forward. As this is done, the ridges 22 and shafts 21 individually engage with the flanges 13c and 13d and annular groove 13b of the receptacle 12, whereby the receptacle 12 is stably and smoothly guided.

According to the transport system 10 of the present embodiment, the screws 20 have the guide and feed functions, so that the parts count can be reduced, the system configuration can be simplified, and the manufacturing costs can be suppressed. Since the screws 20 can be made of molded plastic pieces, moreover, their manufacturing costs can be suppressed. Since the transport does not require the use of a belt, furthermore, belt replacement is unnecessary, so that the maintenance performance is improved, and the necessity of a user's check can be reduced.

In a belt-drive transport system in which a belt is passed around rollers that are arranged along a transport path, the feed function can be achieved by means of screws, although the height of the system increases. Thus, the system can be reduced in height, and hence, in size.

Since the screws 20 are used for the transport, the load of the belt applied to a bearing of a drive shaft in the belt-drive transport system can be mitigated, and the frequency of parts replacement can be reduced.

Each screw 20 has such a simple construction that the continuous helical ridges 22 are arranged on the outer peripheral surface of the shaft 21. Further, the ridge portions 22a that are arranged at regular intervals, as viewed from one lateral side, are configured to axially move at a constant speed as the screw 20 rotates. Therefore, a plurality of receptacles 12 can be accurately transported at a constant speed at regular intervals. Thus, this transport system is particularly excellent as a transport mechanism of a sample processing device for quickly processing a large number of samples with high accuracy.

According to the embodiment described above, moreover, the two simple screws 20 of the same shape should only be rotated at the same speed in the same direction through the transmission mechanism 42 by the common motor 41. Therefore, the control processing and system configuration are simple.

Second Embodiment

Figure 4:
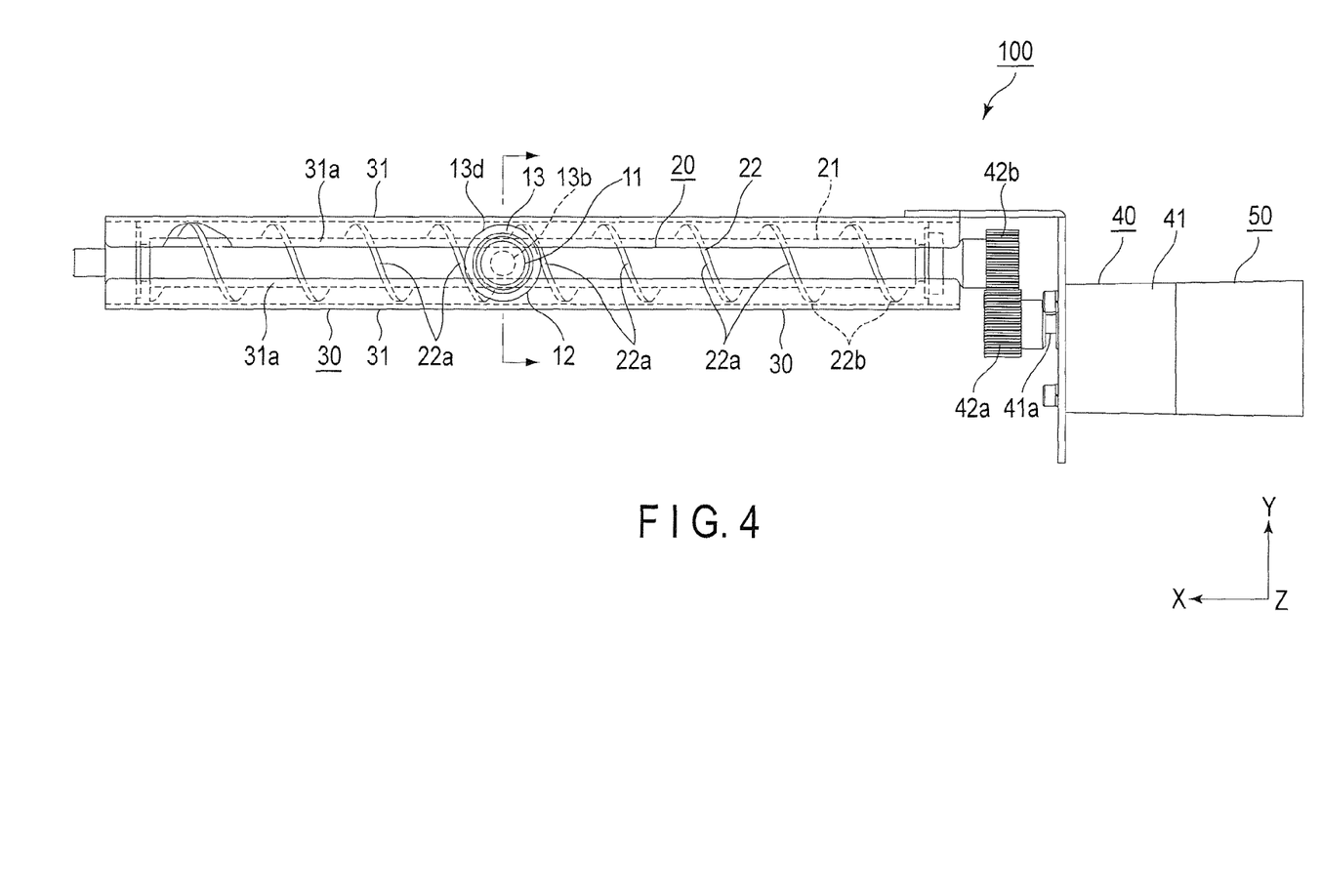
FIG. 4 is a plan view of a transport system according to a second embodiment of the invention.
Figure 5:
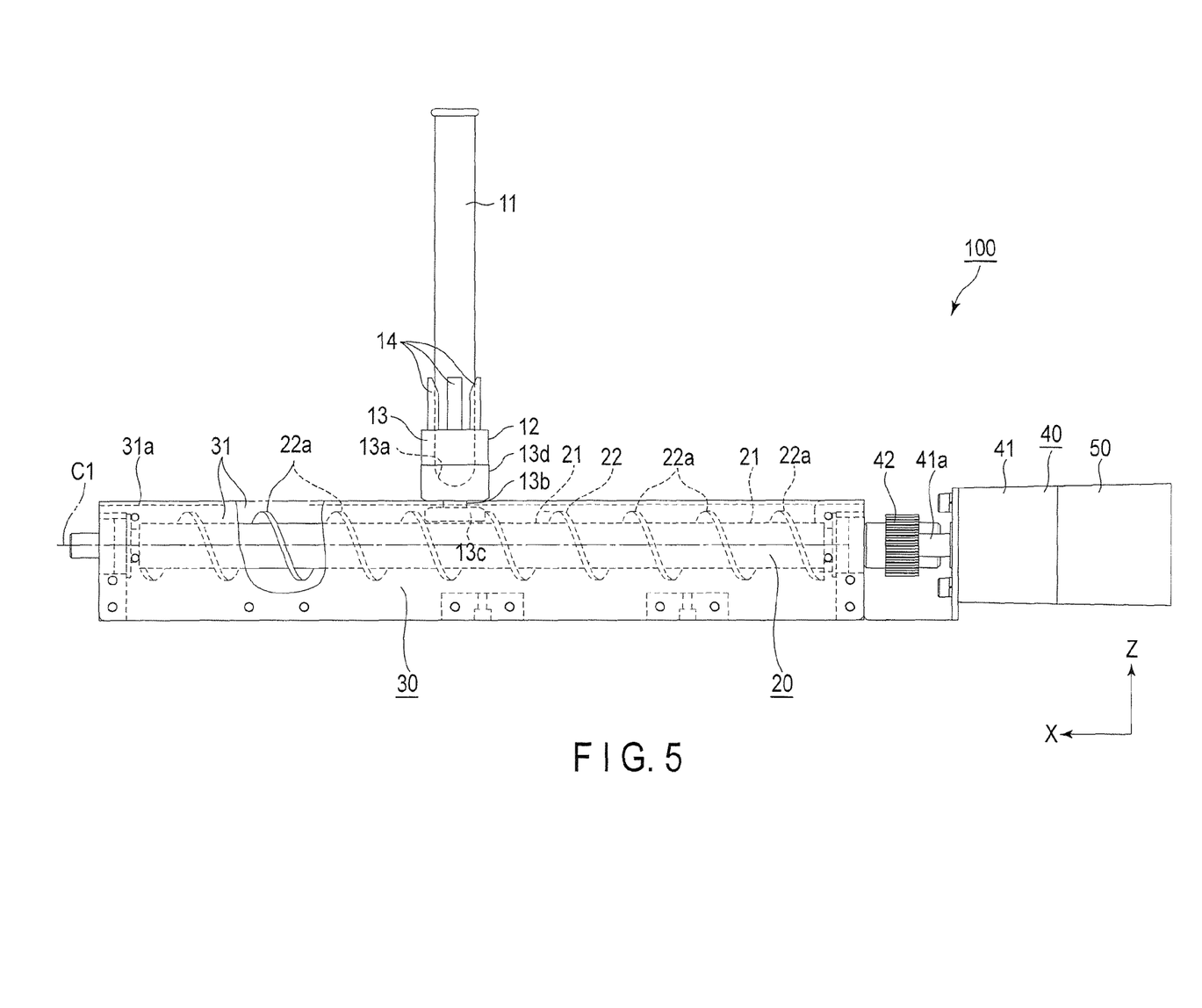
FIG. 5 is a side view of the transport system of the second embodiment.
Figure 6:
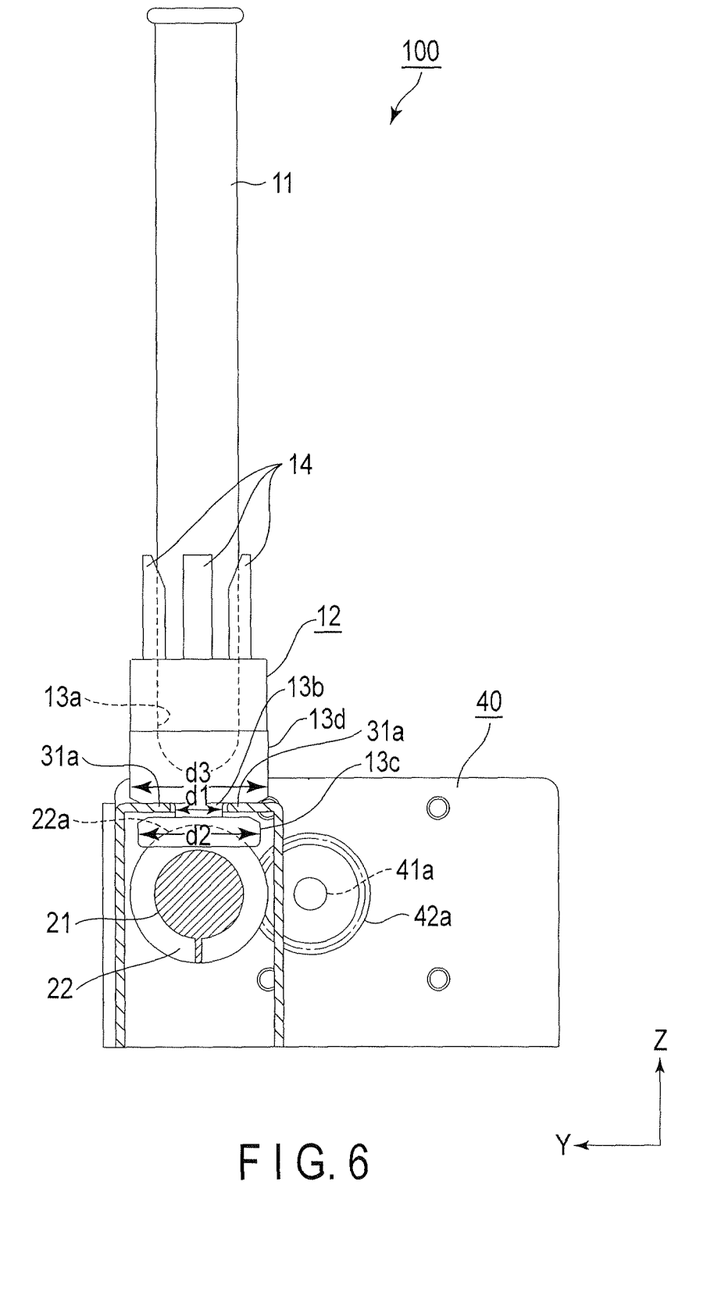
FIG. 6 is a sectional view of the transport system of the second embodiment.

The following is a description of a transport system 100 according to a second embodiment of the invention. FIGS. 4, 5 and 6 and are a plan view, side view, and sectional view, respectively, of the transport system 100 of the present embodiment. In these drawings, some structural elements are enlarged or reduced in scale or omitted for ease of illustration, and arrows X, Y and Z indicate three orthogonal directions, individually.

The transport system 100 according to the present embodiment comprises a single screw 20, frame 30, drive unit 40, and control unit 50. The screw 20 is located extending along a predetermined transport path. The frame 30 comprises a pair of guide rails 31 disposed spaced and supporting the opposite sides of the screw 20. The drive unit 40 serves to rotate the screw 20. The control unit 50 controls the operation of the drive unit 40.

The transport system 100 of this embodiment differs from the transport system 10 of the first embodiment in that a receptacle 12 is supported and transported in engagement between the pair of guide rails 31 at the top part of the single screw 20. Since the structures of individual parts, such as the receptacle 12, screw 20, frame 30, drive unit 40, etc., are the same as those of the transport system 10 of the first embodiment, a description of those parts is omitted.

In the present embodiment, longitudinally extending guide ribs 31a protrude individually inward from the respective upper end edges of the guide rails 31. The distance between the pair of guide ribs 31a is set to be smaller than respective outer diameters d2 and d3 of flanges 13c and 13d and greater than an outer diameter d1 of an annular groove 13b. The receptacle 12 is supported by the frame 30 in such a manner that the guide ribs 31a engage with the annular groove 13b between the flanges 13c and 13d from both sides.

In the transport system 100, the receptacle 12 is set on a shaft 21 of the single screw 20 so that the bottom flange 13c is disposed on the shaft 21. In this state, the bottom flange 13c is held between a plurality of axially arranged ridge portions 22a, and the parallel guide ribs 31a engage with the annular groove 13b between the two flanges 13c and 13d. In this way, the receptacle 12 being transported is supported transversely and axially by the guide ribs 31a and a ridge 22.

The receptacle 12 is axially fed by means of the feed function of the ridge portions 22a based on the rotation of the screws 20. As this is done, the receptacle 12 is guided along the transport path by the guide ribs 31a.

The same effect as in the first embodiment can also be obtained in the present embodiment. Specifically, the screw 20 has guide and feed functions, so that the parts count can be reduced and the system configuration can be simplified. Since the screw 20 is made of a molded plastic piece, moreover, its manufacturing costs can be suppressed. Since the transport does not require the use of a belt, furthermore, belt replacement is unnecessary, so that the maintenance performance is improved, and the necessity of a user's check can be reduced. Further, a plurality of receptacles 12 that are positioned at regular intervals can be accurately transported at a constant speed by the screw 20, so that this transport system is particularly excellent as a transport mechanism of a sample processing device. According to the present embodiment, moreover, the single simple screw 20 should only be rotated, so that the control processing and system configuration can be simplified.

The present invention is not limited directly to the embodiments described herein, and in carrying out the invention, its constituent elements may be embodied in modified forms without departing from the spirit of the invention.

For example, the transport system 10 of the first embodiment is configured so that the annular groove 13b is held between the shafts 21. Alternatively, the transport and guide can be achieved even when the receptacle 12 is placed on the shafts 21 of the transport system 10, as in the transport system 100 of the second embodiment.

Figure 7:
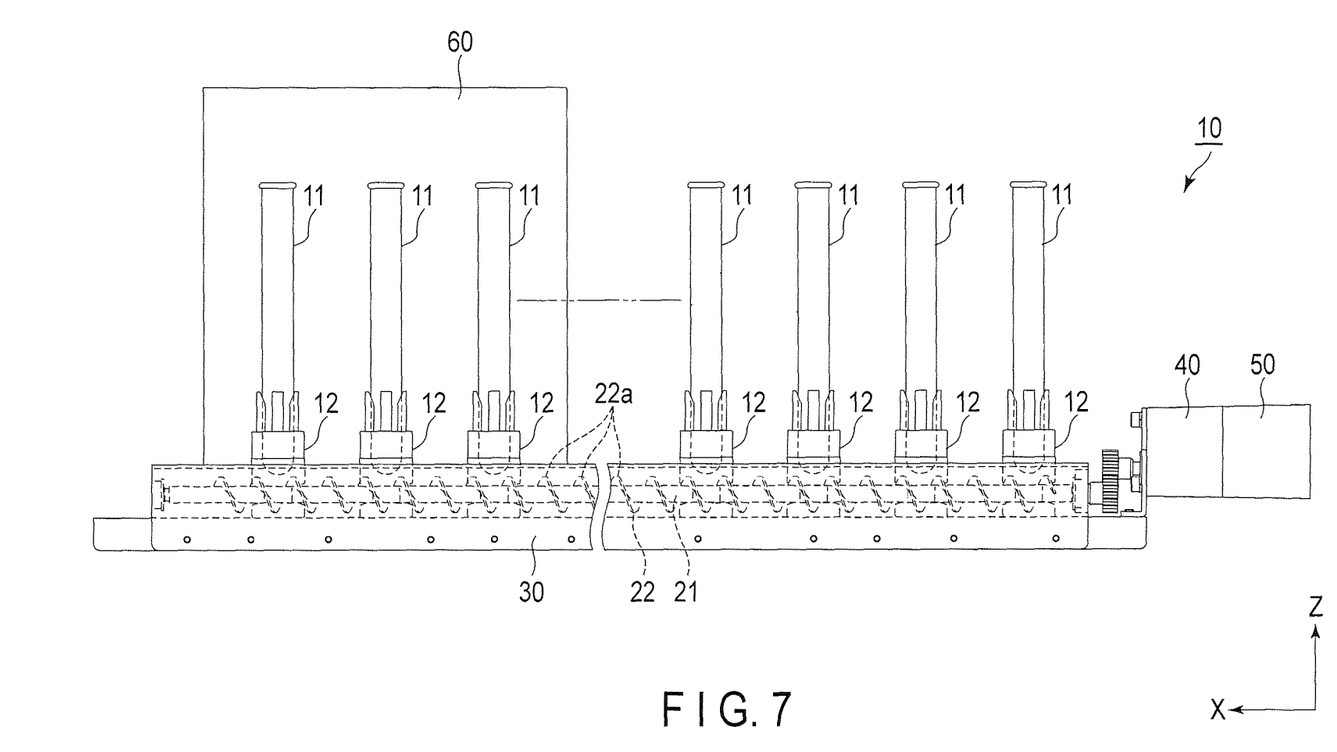
FIG. 7 is a side view of a transport system according to another embodiment.

As in the transport system 10 shown in FIG. 7, for example, a processing device 60 for processing samples, such as an aliquoting/dispensing device, may be disposed along the transport path so that sample holders 11 or samples 11a can be variously processed as the receptacles 12 sequentially fed along the transport path pass through a processing position in the processing device 60.

Further, a plurality of screws 20 may be arranged in a plurality of rows for transport in the transport systems 10 and 100. Furthermore, a plurality of screws 20 or a plurality of transport systems 10 and 100 may be continuously disposed along the transport path so that the transport path varies in transport direction or comprises bent portions, for example.

In addition, the constituent elements described in connection with the foregoing embodiments may be deleted or their shapes, structures, materials, etc., may be changed. Various inventions may be made by suitably combining a plurality of constituent elements described in connection with the foregoing embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A transport system configured to transport a receptacle which accommodates an upright sample holder containing a sample, comprising:
    a pair of screws arranged parallel to each other, each of the screws comprising a rotatable-shaft disposed along a predetermined transport path and a helical ridge protruding outward from an outer peripheral surface of the shaft, the ridge comprising a plurality of ridge portions being arranged along an axial direction in the outer peripheral surface of the shaft;
    a drive unit configured to rotate the screw; and
    the receptacle,
    wherein the receptacle comprises an inwardly recessed groove section on an outer peripheral surface thereof and flanges protruding outward from the groove section and located below and above, respectively, of the groove section,
    the groove section is sandwiched between the shafts of the pair of screws, and
    the lower and upper flanges are sandwiched between the ridge portions axially arranged on the pair of screws.

2. A transport method capable of transporting a receptacle which accommodates an upright sample holder containing a sample, comprising:
    rotating a pair of screws arranged parallel to each other, each of the screws comprising a rotatable shaft disposed along a predetermined transport path and a helical ridge protruding outward from an outer peripheral surface of the shaft, the pair of screws being configured to sandwich inwardly recessed groove section formed on an outer peripheral surface of the receptacle between the shafts, and sandwich flanges protruding outward from the groove section and located below and above, respectively, of the groove section between the ridge portions arranged in the axial direction; and
    feeding the receptacle held between the ridge portions along the transport path.

* * * * *